(12) United States Patent  
Lim et al.

(10) Patent No.: US 8,080,035 B2
(45) Date of Patent: Dec. 20, 2011

(54) SUTURE ATTACHMENT DEVICE (75) Inventors: Jyue Boon Lim, New Brighton, MN (US); Gary James Schorr, Apple Valley, MN (US)

(73) Assignee: St. Jude Medical, Cardiology Division, Inc., Minnetonka, MN (US)

(*) Notice: Subject to any disclaimer, the term of this patent is extended or adjusted under 35 U.S.C. 154(b) by 284 days.

(21) Appl. No.: 11/551,642

(22) Filed: Oct. 20, 2006

(65) Prior Publication Data

US 2008/0097527 A1   Apr. 24, 2008

(51) Int. Cl.
*A61B 17/04* (2006.01)
(52) U.S. Cl. ........................................ 606/232
(58) Field of Classification Search ............... 623/13.14; 606/232
See application file for complete search history.

(56) References Cited

U.S. PATENT DOCUMENTS

| | | | |
|---|---|---|---|
| 5,084,058 A | 1/1992 | Li | |
| 5,324,298 A | 6/1994 | Phillips et al. | |
| 5,364,408 A | 11/1994 | Gordon | |
| 5,458,609 A | 10/1995 | Gordon et al. | |
| 5,496,348 A * | 3/1996 | Bonutti | 606/232 |
| 5,562,684 A | 10/1996 | Kammerer | |
| 5,643,292 A | 7/1997 | Hart | |
| 5,797,928 A | 8/1998 | Kogasaka | |
| 5,845,645 A * | 12/1998 | Bonutti | 128/898 |
| 5,868,762 A | 2/1999 | Cragg et al. | |
| 5,984,933 A | 11/1999 | Yoon | |
| 5,993,459 A * | 11/1999 | Larsen et al. | 606/104 |
| 6,059,800 A | 5/2000 | Hart et al. | |
| 6,074,395 A | 6/2000 | Trott et al. | |
| 6,132,439 A | 10/2000 | Kontos | |
| 6,283,947 B1 | 9/2001 | Mirzaee | |
| 6,358,259 B1 | 3/2002 | Swain et al. | |
| 6,533,795 B1 | 3/2003 | Tran et al. | |
| 6,702,825 B2 | 3/2004 | Frazier et al. | |
| 6,716,224 B2 | 4/2004 | Singhatat | |
| 6,855,124 B1 | 2/2005 | Gonzalez et al. | |
| 7,160,309 B2 | 1/2007 | Voss | |
| 7,226,467 B2 | 6/2007 | Lucatero et al. | |
| 2003/0040712 A1 | 2/2003 | Ray et al. | |
| 2003/0181926 A1 | 9/2003 | Dana et al. | |
| 2004/0068273 A1 | 4/2004 | Fariss et al. | |
| 2004/0097973 A1 | 5/2004 | Loshakove et al. | |
| 2005/0159812 A1* | 7/2005 | Dinger et al. | 623/13.14 |
| 2007/0203507 A1 | 8/2007 | McLaughlin et al. | |
| 2008/0033459 A1 | 2/2008 | Shafi et al. | |
| 2008/0097479 A1 | 4/2008 | Boehlke et al. | |
| 2008/0097480 A1 | 4/2008 | Schorr et al. | |
| 2008/0097481 A1 | 4/2008 | Schorr et al. | |
| 2008/0097484 A1 | 4/2008 | Lim et al. | |

* cited by examiner

*Primary Examiner* — Melanie Tyson
*Assistant Examiner* — Son Dang
(74) *Attorney, Agent, or Firm* — Holland & Hart (57) ABSTRACT

A suture attachment device for fastening multiple suture filaments at a wound or surgical site is provided. In one embodiment, the suture attachment device comprises a lock body having a proximal surface and a distal surface and extending along a longitudinal axis. The lock body includes at least two passageways defined between the proximal surface and the distal surface. Each of the passageways are sized and shaped for receiving a suture filament.

11 Claims, 9 Drawing Sheets

SUTURE ATTACHMENT DEVICE

FIELD OF THE INVENTION

This invention relates generally to surgical devices, and more specifically to a suture attachment device for fastening or tightening multiple individual sutures over a wound and method of using such device.

BACKGROUND OF THE INVENTION

In order to close an incision, surgeons often use retention sutures. These sutures are typically held in place by a knot or by suture attachment devices. Presently, there are no suture attachment devices capable of fastening multiple suture filaments.

BRIEF SUMMARY OF THE INVENTION

A suture attachment device for fastening multiple suture filaments at a wound or surgical site is provided.

In one embodiment, the suture attachment device comprises a lock body having a proximal surface and a distal surface and extending along a longitudinal axis. The lock body includes at least two passageways defined between the proximal surface and the distal surface. Each of the passageways are sized and shaped for receiving a suture filament.

In another embodiment the suture attachment device comprises a base element and a crimp. The base element includes a proximal side and a distal side. An internal cavity extends though the base element along the longitudinal axis. The base element further includes a plurality of entrance apertures through which the suture to enter the base element and an exit aperture through which the suture to exit the base element. The crimp retains the suture to the base element as threaded through the entrance apertures and the exit aperture.

While multiple embodiments are disclosed, still other embodiments of the invention will become apparent to those skilled in the art from the following detailed description, which shows and describes illustrative embodiments of the invention. As will be realized, the invention is capable of modifications in various obvious aspects, all without departing from the spirit and scope of the invention. Accordingly, the drawings and detailed description are to be regarded as illustrative in nature and not restrictive.

DETAILED DESCRIPTION OF THE INVENTION

A suture attachment device for fastening multiple suture filaments at a wound or surgical site is provided. The suture attachment device, or suture lock, may be used to fasten multiple suture filaments to seal a vascular access wound. It should be appreciated by those skilled in the art, however, the suture attachment device may be used in a variety of situations to seal any suitable wound, incision, puncture, or suture site.

Figure 1:
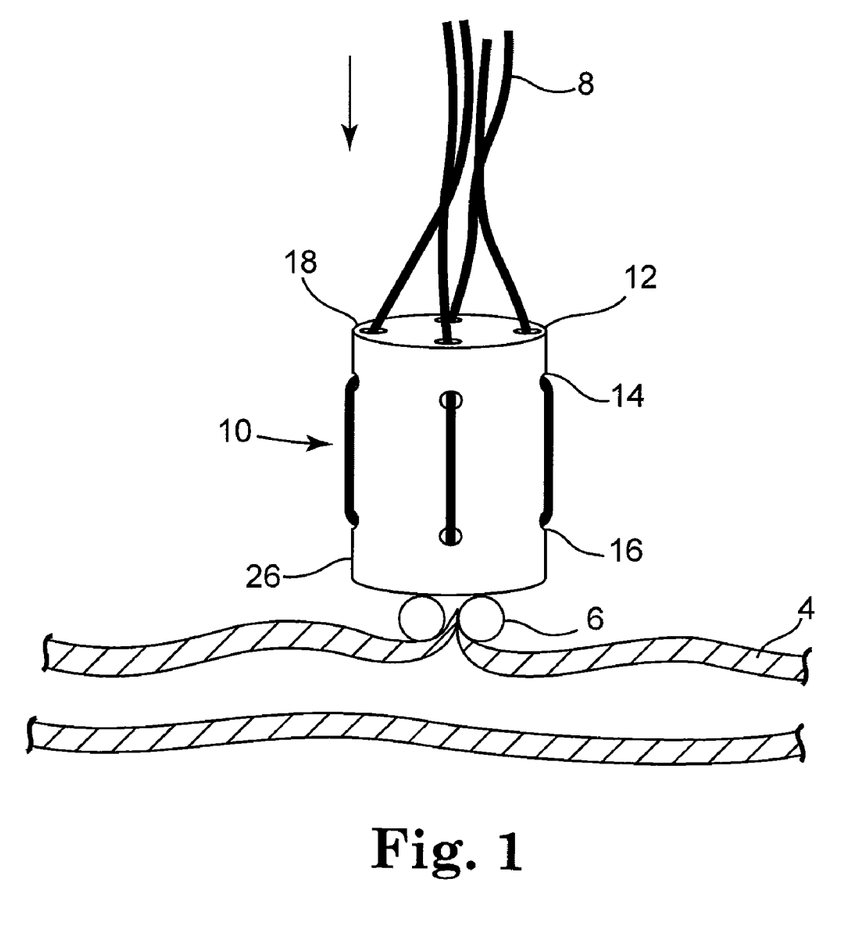
FIG. 1 is a perspective view of an lock body of a suture attachment device deployed at a vascular puncture in accordance with one embodiment.
Figure 2:
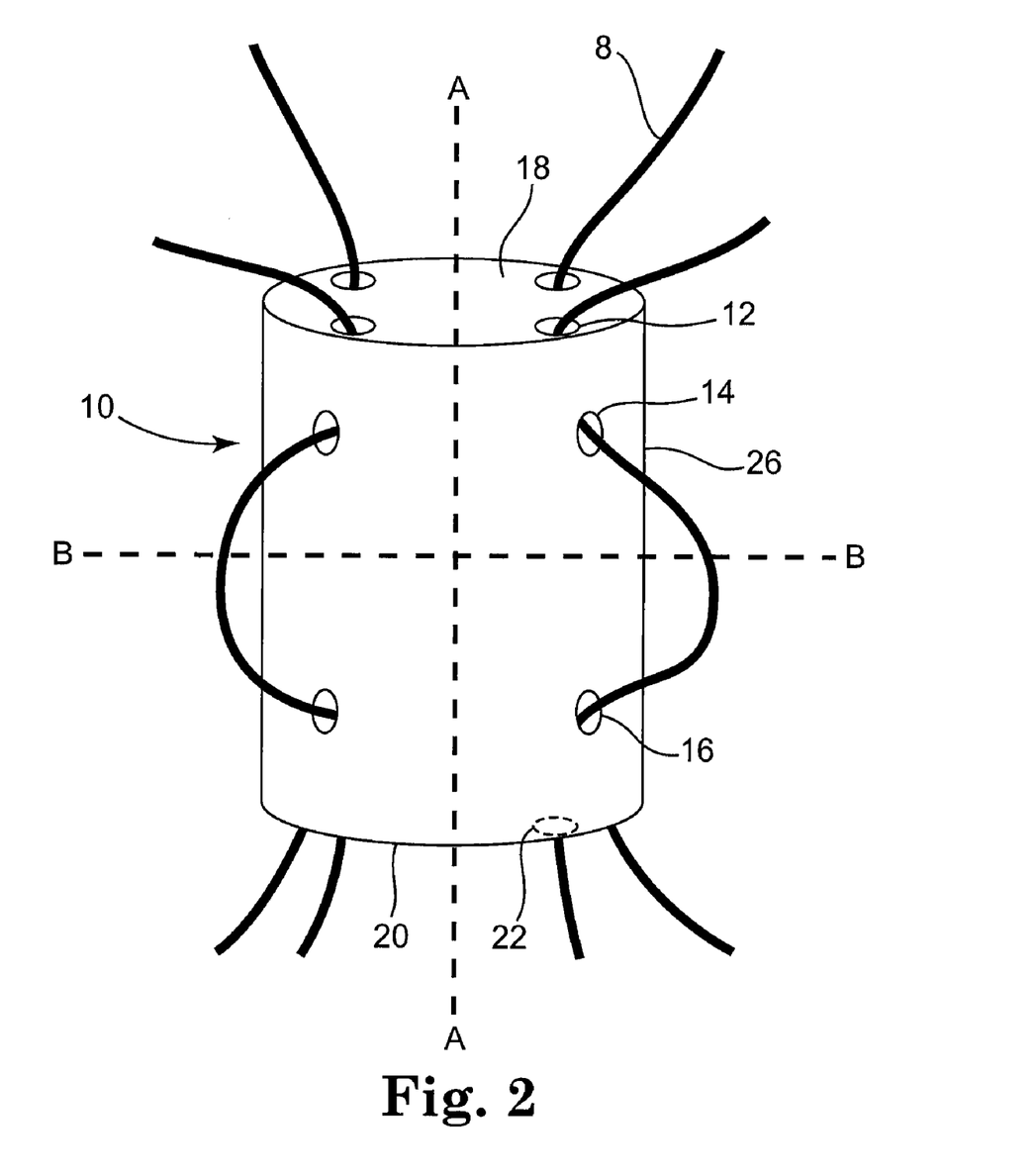
FIG. 2 is a perspective view of an lock body of a suture attachment device in accordance with one embodiment.
Figure 3:
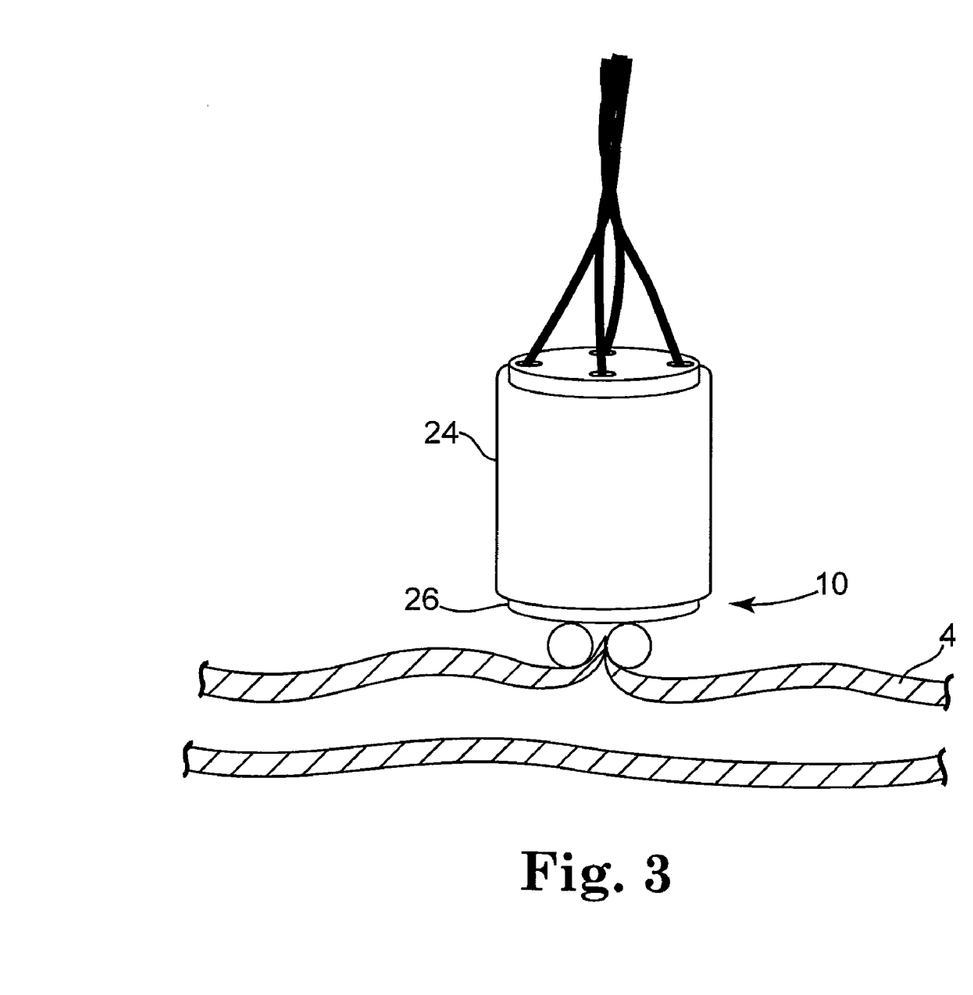
FIG. 3 is a perspective view of an outer sleeve of a suture attachment device deployed over an lock body of a suture attachment device deployed at a vascular puncture in accordance with one embodiment.

A first embodiment of the suture attachment device is shown in FIGS. 1 through 3. As shown, the suture attachment device 5 (or suture lock) includes an lock body 10 and, optionally, an outer sleeve 24. Either or both of the lock body 10 and the outer sleeve 24 may be manufactured as a molded or machined bioabsorbable material or an implant grade polymer. Alternatively, the lock body 10 and the outer sleeve 24 may be any suitable material manufactured in any suitable manner. Generally, the lock body 10 is manufactured of an elastic material such that the lock body 10 has a flexible or nonrigid characteristic. In one embodiment, the lock body 10 and the outer sleeve 24 are flexible such that they conform around the sutures to wrap the sutures. In some embodiments, the sleeve 24 is more flexible than the lock body 10. The lock body 10 and the outer sleeve 24 have complementary shapes such that the lock body 10 receive the outer sleeve 24 therearound, as is described more fully below. It should be noted that it is not necessary that the lock body 10 and the outer sleeve 24 have identical shapes. In the embodiment shown, both the lock body 10 and the outer sleeve 24 are substantially cylindrical. Alternatively, either or both of the lock body 10 and the outer sleeve 24 may be rectangular, spherical, or otherwise shaped. The lock body 10 extends along a longitudinal axis (axis line B-B of FIG. 2), substantially perpendicular to a radial axis (axis line A-A of FIG. 2). With particular reference to FIG. 2, the lock body 10 includes a proximal surface 18 (farthest away from the vascular puncture) and a distal surface 20 (closest to the vascular puncture). One or more proximal surface passageways 12 are provided on the proximal surface 18. One or more distal surface passageways 22 are provided on the distal surface 20. In the embodiment shown, the lock body 10 includes four proximal surface passageways 12 and four distal surface passageways 22. In alternative embodiments, more or fewer proximal surface passageways 12 or distal surface passageways 22 may be provided. In the embodiment shown, an equal number of proximal surface passageways 12 is provided as distal surface passageways 22. In alternative embodiments, the number of proximal surface passageways 12 and the number of distal surface passageways 22 may not be equal.

One or more proximal apertures 14 are provided on an external wall 26 of the lock body 10. Each proximal surface passageway 12 extends from the proximal surface 18 to the proximal aperture 14. In the embodiment shown, one proximal aperture 14 is provided for each proximal surface passageway 12. In alternative embodiments, a plurality of proximal surface passageways 12 may extend to a single proximal aperture 14. Alternatively, a plurality of proximal apertures 14 may lead to a single proximal surface passageway 12.

One or more distal apertures 16 are provided on an external wall 26 of the lock body 10. Each distal surface passageway 22 extends from the distal surface 20 to the distal aperture 16. In the embodiment shown, one distal aperture 16 is provided for each distal surface passageway 22. In alternative embodiments, a plurality of distal surface passageways 22 may extend to a single distal aperture 16. Alternatively, a plurality of distal apertures 16 may lead to a single distal surface passageway 22. Generally, the diameter of each of the proximal surface passageways 12, the distal surface passageways 22, the proximal apertures 14, and the distal apertures 16 is sufficient to accommodate a suture filament 8. Thus, the diameter of the proximal surface passageways 12, the distal surface passageways 22, the proximal apertures 14, and the distal apertures 16 may be slightly greater than or slightly less than the outside diameter of suture filament 8. In one embodiment, the diameter of the proximal surface passageways 12, the distal surface passageways 22, the proximal apertures 14, and the distal apertures 16 may be between approximately 2% and approximately 50% larger or smaller than the outside diameter of the suture filament 8, for example approximately 33% larger or smaller than the outside diameter of the suture filament 8.

The lock body 10 receives a plurality of suture filaments 8 to fasten the filaments 8. The suture filaments are threaded through the proximal surface passageways 12 and the distal surface passageways 22. The proximal and distal surface passageways 12, 20 are shown in FIGS. 1 and 2 being spaced apart and isolated from each other. A pathway for a suture filament 8 from the proximal surface 18 to the distal surface 20 through a first set of proximal and distal surface passageways 12, 22 is shown in FIGS. 1 and 2 as being separate and distinct from a pathway for another suture filament 8 extending through a second set of proximal and distal surface passageways 12, 22. The suture filaments may be threaded through the lock body 10 in any suitable manner. For the purposes of illustration, the threading is described with first threading through the proximal surface passageways 12 and then through the distal surface passageways 22. Accordingly, a suture filament 8 is threaded into a proximal surface passageway 12 and out a proximal aperture 14, extended over a portion of the external wall 26, threaded into a distal aperture 16 and out a distal surface passageway 22. The proximal surface passageway 12 and the distal surface passageway 22 together allow for the translational movement of the lock body 10 with respect to the suture filament 8. One or more filaments 8 may be threaded through each set of proximal surface passageways 12, proximal apertures 14, distal apertures 16, and distal surface passageways 22. Again, a single proximal aperture 14 or distal aperture 16 may be provided for a plurality of proximal passageways 12 or distal passageways 22, respectively. Further, a single passageway including a proximal portion and a distal portion may be provided extending between a proximal aperture 14 and a distal aperture 16.

The positioning of the suture filaments 8 within the body 10 once threaded can be varied to control resistance of the suture filaments 8. For example, the path of the suture filaments 8 through the body 10 may be longer or shorter, more or less tortuous, etc. Resistance of the suture filaments 8 to the lock body 10 contributes to the ease of deployment of the suture filaments 8 and the ability of the suture filaments 8 to stay in place once the lock body 10 is deployed.

In the embodiment illustrated in FIGS. 1 through 3, the proximal surface passageway 18 and distal surface passageway 22 are aligned with respect to the radial axis (A-A) of the lock body 10. In alternative embodiments, the proximal surface passageway 18 and the distal surface passageway 22 may be offset, for example by an acute angle with respect to the radial axis (A-A) of the lock body 10. This embodiment allows for more surface area over which the sutures travel which, in turn, provides more drag force.

As shown in FIG. 1, an anchor 6 is deployed at a vascular puncture 2 of an artery 4. The anchor 6 may comprise a suture or may comprise a separate device coupled to a suture. In the embodiment shown, the anchor 6 comprises a metal anchor such as a needle coupled to a suture filament 8. A plurality of anchors and associated suture filaments may be used to close a single vascular puncture. In the embodiment shown, four anchors 6 and associated suture filaments 8 are used. Obviously, any suitable number of anchors and or filaments may be used. The suture filaments 8 extend from the anchor, through the distal surface passageway 22, through the distal aperture 16, over the external wall 26, through the proximal aperture 14, and out the proximal surface passageway 12.

After the anchor 6 has been deployed but before the lock body 10 is deployed, the lock body 10 is positioned proximally of the anchor 6. As a pushing force is applied against the lock body 10 in the direction of the arrow (see FIG. 1), the lock body 10 is driven along the suture filaments 8, until the lock body 10 contacts with the vascular puncture 2, or until force is no longer applied. A pusher may be used to apply the pushing force to the lock body 10. As described with reference to FIG. 10, a suture knot system 300 may be used to deploy the lock body 10 and to keep the sutures in tension, for example by pulling the sutures taut proximally.

The drag force or friction created by contact of each suture filament 8 with proximal surface passageway 12, distal surface passageway 22, and external wall 26 is sufficient to retain the lock body 10 in contact with the vascular puncture 2.

However, to ensure secure positioning of the lock body 10 at the vascular puncture 2, an outer sleeve 24 may be deployed over the lock body 10. FIG. 3 illustrates the outer sleeve 24 deployed over the lock body 10. Once the lock body 10 is in contact with the vascular puncture 2, the suture sleeve 24 may be slidably placed over the lock body 10. The suture sleeve 24 is frictionally engaged with the external wall 26 of the lock body 10. This frictional engagement provides additional resistance to retain the lock body 10 in contact with the vascular puncture. The outer sleeve 24 may be sized and configured to snugly fit over the lock body 10 and suture filaments 8 extending over the external wall 26 of the lock body 10. In various embodiments, an outer sleeve is not used.

Figure 4:
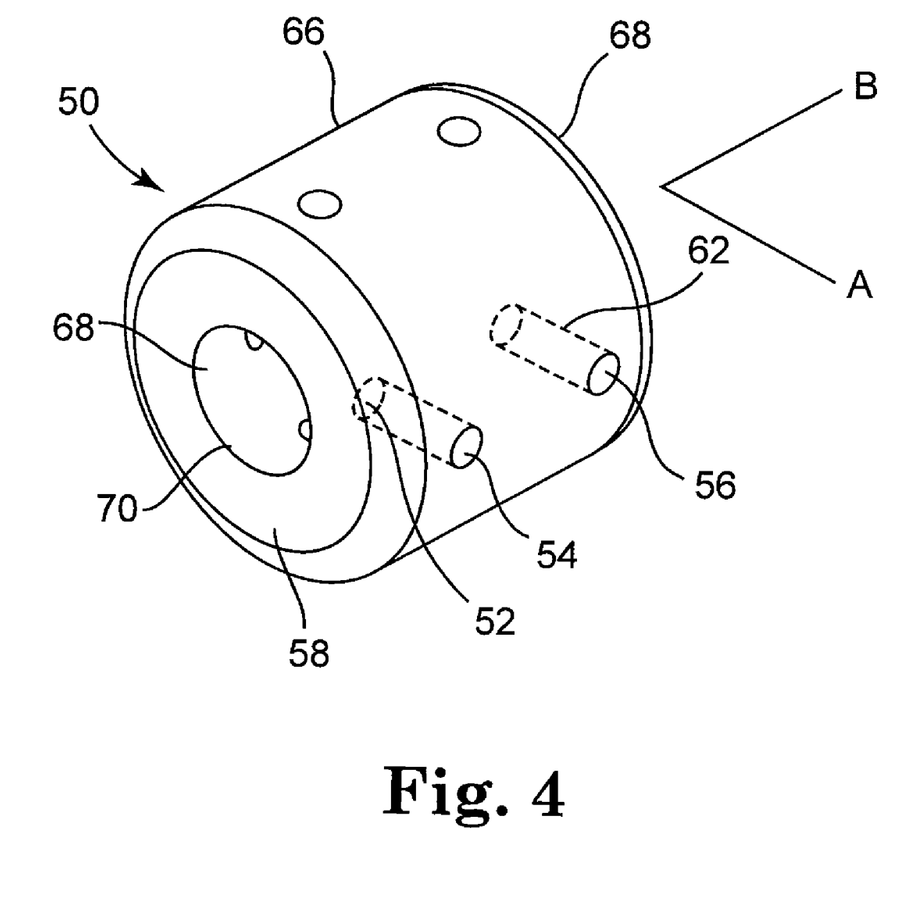
FIG. 4 is a perspective view of an lock body of a suture attachment device in accordance with a further embodiment.
Figure 5:
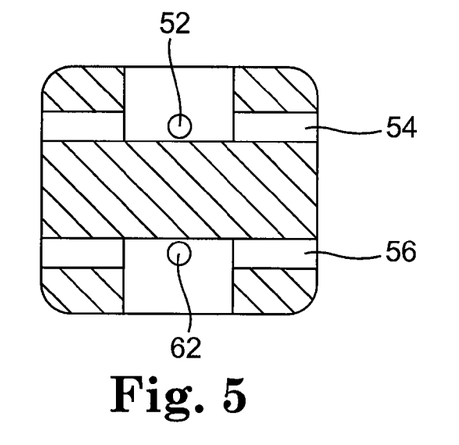
FIG. 5 is a side cross sectional view of the lock body of FIG. 4.

FIGS. 4 and 5 illustrate an alternate embodiment of a suture attachment device. The suture attachment device comprises a lock body 50. The lock body 50 may comprise a molded piece of bioabsorbable material. As shown, the lock body 50 is substantially cylindrical. Alternatively, the lock body 50 may be rectangular, spherical, or otherwise shaped. The lock body extends along a longitudinal axis (axis line B) which is substantially perpendicular to a radial axis (axis line A).

The lock body 50 has a proximal surface 58 (farthest away from the vascular puncture) and a distal surface 60 (closest to the vascular puncture). An internal cavity is provided within the lock body 50, extending the lock body 50 substantially along the longitudinal axis (axis line B). The internal cavity 68 has an internal cavity wall 70. Defined in the internal cavity wall 70 is at least one proximal passageway 52 and at least one distal passageway 62. In the embodiment shown, four proximal passageways 52 and four distal passageways 62 are provided. More or fewer proximal passageways 52 and distal passageways 62 may be provided and the number of proximal passageways 52 and the number of distal passageways 62 need not be equal.

The proximal passageway 52 terminates in a proximal aperture 54 defined in an external wall 66 of the lock body 50.

In the embodiment shown, one proximal aperture 54 is provided for each proximal passageway 12. In alternative embodiments, a plurality of proximal passageways 52 may extend to a single proximal aperture 54. Alternatively, a plurality of proximal apertures 54 may lead to a single proximal passageway 52.

The distal passageway 62 terminates in a distal aperture 56 defined in the external wall 66 of the lock body 50. In the embodiment shown, one distal aperture 56 is provided for each distal passageway 62. In alternative embodiments, a plurality of distal passageways 52 may extend to a single distal aperture 56. Alternatively, a plurality of distal apertures 56 may lead to a single distal passageway 62. Generally, the diameter of each of the proximal passageways 52, the distal passageways 62, the proximal apertures 54, and the distal apertures 56 is sufficient to accommodate a suture filament 8. Thus, the diameter of the proximal surface passageways 52, the distal surface passageways 62, the proximal apertures 54, and the distal apertures 56 may be slightly greater than or slightly less than the outside diameter of suture filament 8.

The lock body 50 receives a plurality of suture filaments 8 to fasten the filaments 8. The suture filaments are threaded through the proximal passageways 52 and the distal surface passageways 62. The order of threading before use is not of importance. However, for the purposes of illustration, the threading is described with first threading through the proximal passageways 52 and then through the distal passageways 62. Accordingly, a suture filament 8 is threaded into a proximal passageway 52 and out a proximal aperture 54, extended over a portion of the external wall 66, threaded into a distal aperture 56 and out a distal passageway 62. The proximal passageway 52 and the distal passageway 62 together allow for the translational movement of the lock body 50 with respect to the suture filament 8. One or more filaments 8 may be threaded through each set of proximal passageways 52, proximal apertures 54, distal apertures 56, and distal passageways 62. Again, a single proximal aperture 54 or distal aperture 56 may be provided for a plurality of proximal passageways 52 or distal passageways 62, respectively. Similarly, a single proximal passageway 52 or distal passageway 62 may be provided for a plurality of proximal apertures 54 or distal apertures 56, respectively.

The positioning of the suture filaments 8 within the body 50 once threaded can be varied to control resistance of the suture filaments 8. For example, the path of the suture filaments 8 through the body 50 may be longer or shorter, more or less tortuous, etc. Resistance of the suture filaments 8 to the lock body 50 contributes to the ease of deployment of the suture filaments 8 and the ability of the suture filaments 8 to stay in place once the lock body 50 is deployed.

The suture lock device of FIGS. 4 and 5 is deployed in the same manner as that of FIGS. 1 through 3. An anchor is deployed at a vascular puncture of an artery. The anchor may comprise a suture or may comprise a separate device, such as a needle, coupled to a suture. Suture filaments 8 extend from the anchor, through the distal passageway 62, through the distal aperture 56, over the external wall 66, through the proximal aperture 54, and out the proximal passageway 52.

After the anchor has been deployed but before the lock body 50 is deployed, the lock body 50 is positioned proximally of the anchor. As a pushing force is applied against the lock body 50 towards the vascular puncture site, the lock body 50 is driven along the suture filaments 8, until the lock body 50 contacts with the vascular puncture, or until force is no longer applied. This pushing force, in turn, forces the wound to come together and provides an approximate sealing of the vascular wound. Before, during, or after suture lock device deployment, the physician may apply manual compression to the surgical site to reduce bleeding. A pusher may be used to apply the pushing force to the lock body 50.

The drag force or friction created by contact of each suture filament 8 with proximal passageway 52, distal passageway 62, and external wall 66 is sufficient to retain the lock body 50 in contact with the vascular puncture. However, to ensure secure positioning of the lock body 50 at the vascular puncture 2, an outer sleeve, similar to outer sleeve 24 of FIG. 3, may be deployed over the lock body 50.

In the embodiment illustrated in FIGS. 4 and 5, the proximal passageway 52 and distal passageway 62 are aligned with respect to the radial axis (A) of the lock body 50. In alternative embodiments, the proximal passageway 52 and the distal passageway 62 may be offset, for example by an acute angle with respect to the radial axis (A) of the lock body 50. This embodiment allows for more surface area over which the sutures travel which, in turn, provides more drag force.

Figure 6:
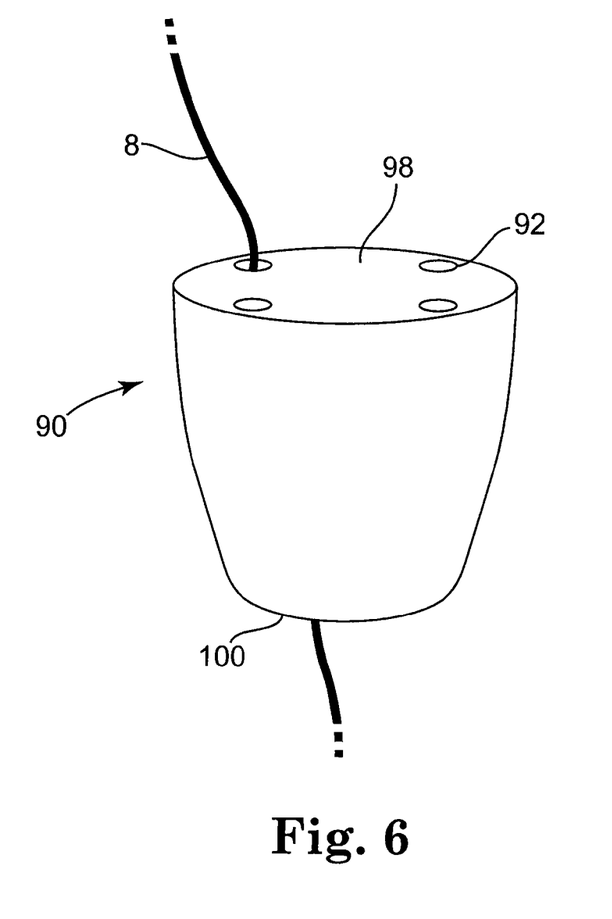
FIG. 6 is a perspective view of an lock body of a suture attachment device in accordance with yet another embodiment.
Figure 7:
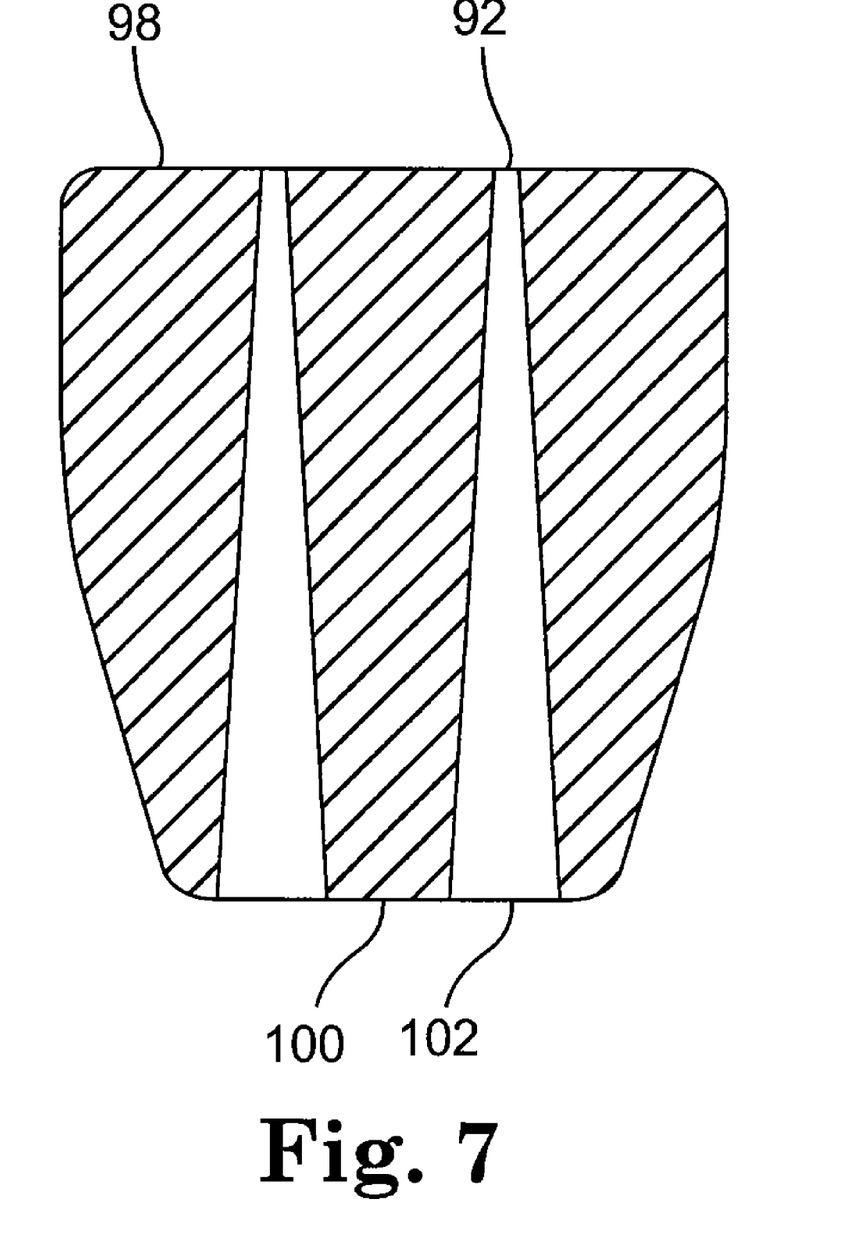
FIG. 7 is a cross sectional view of the lock body of FIG. 6.

FIGS. 6 and 7 illustrate a further embodiment of a suture lock device. The suture lock device comprises a lock body 90. The lock body 90 may comprise a molded piece of bioabsorbable material or may alternatively comprise any suitable material manufactured in any suitable manner. As depicted in FIG. 6, the lock body 90 comprises a tapered cylinder. The cylinder tapers at its distal end (closest to the vascular puncture) to enable easy traveling into subcutaneous tissue. In alternative embodiments, the lock body 90 may not be tapered. Further, the lock body 90 may be provided in any suitable shape and may be round, flat, spherical, rectangular, or other. The lock body 90 extends along a longitudinal axis which is substantially perpendicular to a radial axis.

The lock body 90 includes a proximal surface 98 (farthest away from the vascular puncture) and a distal surface 100 (closest to the vascular puncture). At least one proximal surface passageway 92 is provided on the proximal surface 98 while at least one distal surface aperture 102 is provided on the distal surface 100. As shown, each proximal surface passageway 92 extends to a corresponding distal surface aperture 102. In the embodiment illustrated in FIG. 6, there are four proximal surface passageways 92 and four distal surface apertures 102. In alternative embodiments, more or fewer proximal surface passageways 92 and more or fewer distal surface apertures 102 may be provided. Further, the number of proximal surface passageways 92 and the number of distal surface apertures 102 need not be equal. Thus, for example, a plurality of proximal surface passageways 92 may terminate in a single distal surface aperture 102. FIG. 7 illustrates a schematic cross section of the suture lock device 90. As shown, each proximal surface passageway 92 terminates in a distal surface aperture 102.

Generally, the diameter of each of the proximal surface passageways 92 and the distal surface apertures 102 is sufficient to accommodate a suture filament 8. Thus, the diameter of the proximal surface passageways 92 and the distal surface apertures 102 may be slightly greater than the outside diameter of suture filament 8. As shown, the diameter of the proximal surface passageway 92, however, increases as it passes through the suture lock device 90, terminating in a maximum diameter at distal surface aperture 102.

An anchor is deployed at a vascular puncture of an artery. The anchor may comprise a suture, such as a suture knot, or may comprise a separate device, such as a needle, coupled to a suture. Suture filaments 8 extend from the anchor, through the distal surface aperture 102 and out the proximal surface passageway 92. After the anchor has been deployed but before the lock body 90 is deployed, the lock body 90 is positioned proximally of the anchor. As a pushing force is applied against the lock body 90 towards the vascular puncture site, the lock body 90 is driven along the suture filaments 8, until the lock body 90 contacts with the vascular puncture, or until force is no longer applied. A pusher may be used to apply the pushing force to the lock body 90.

The proximal surface passageways 92 allow for the translational movement of the suture lock device 90 with respect to the suture filament 8. Once the suture lock device 90 is in contact with a vascular puncture, the drag force created by contact of suture filament 8 with proximal passageway 92 is sufficient to retain the suture lock device 90 in contact with the vascular puncture.

Figure 8:
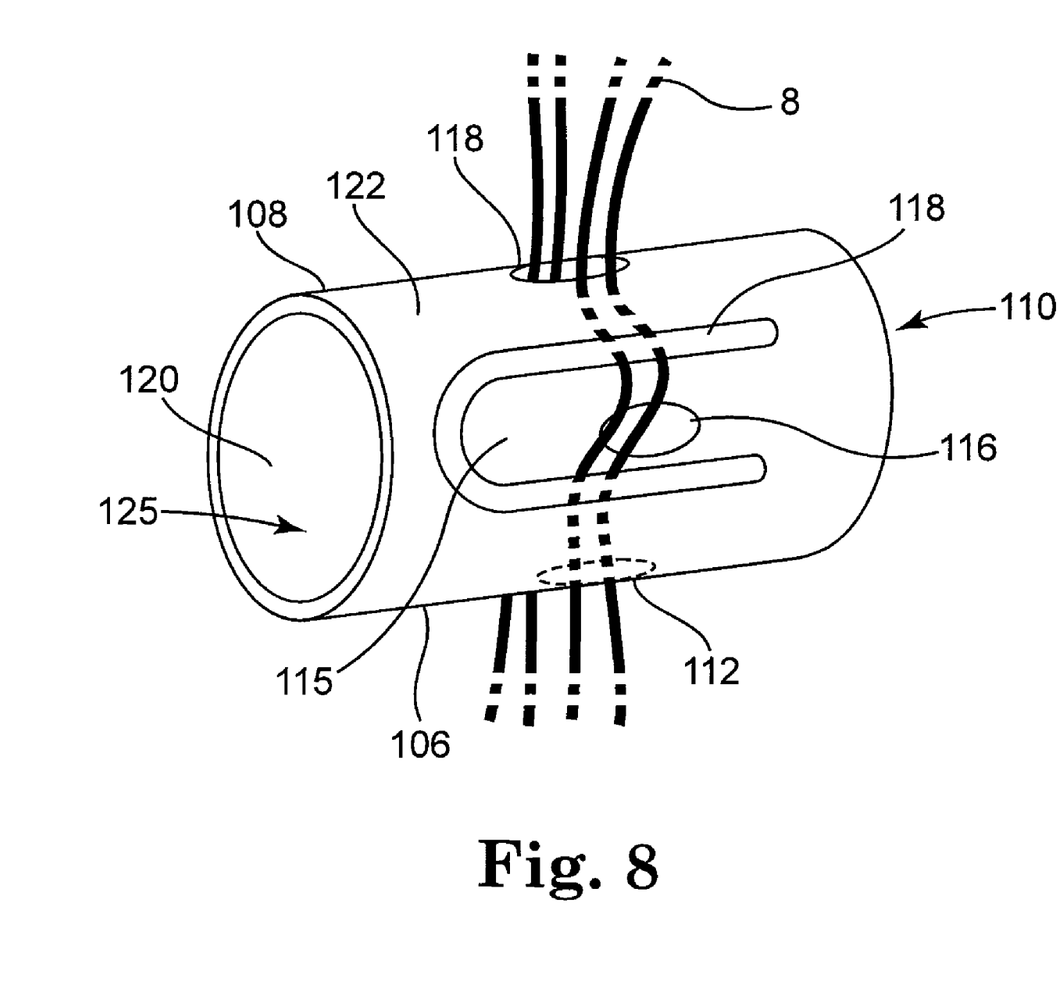
FIG. 8 is a perspective view of a suture attachment device in accordance with yet a further embodiment.
Figure 9:
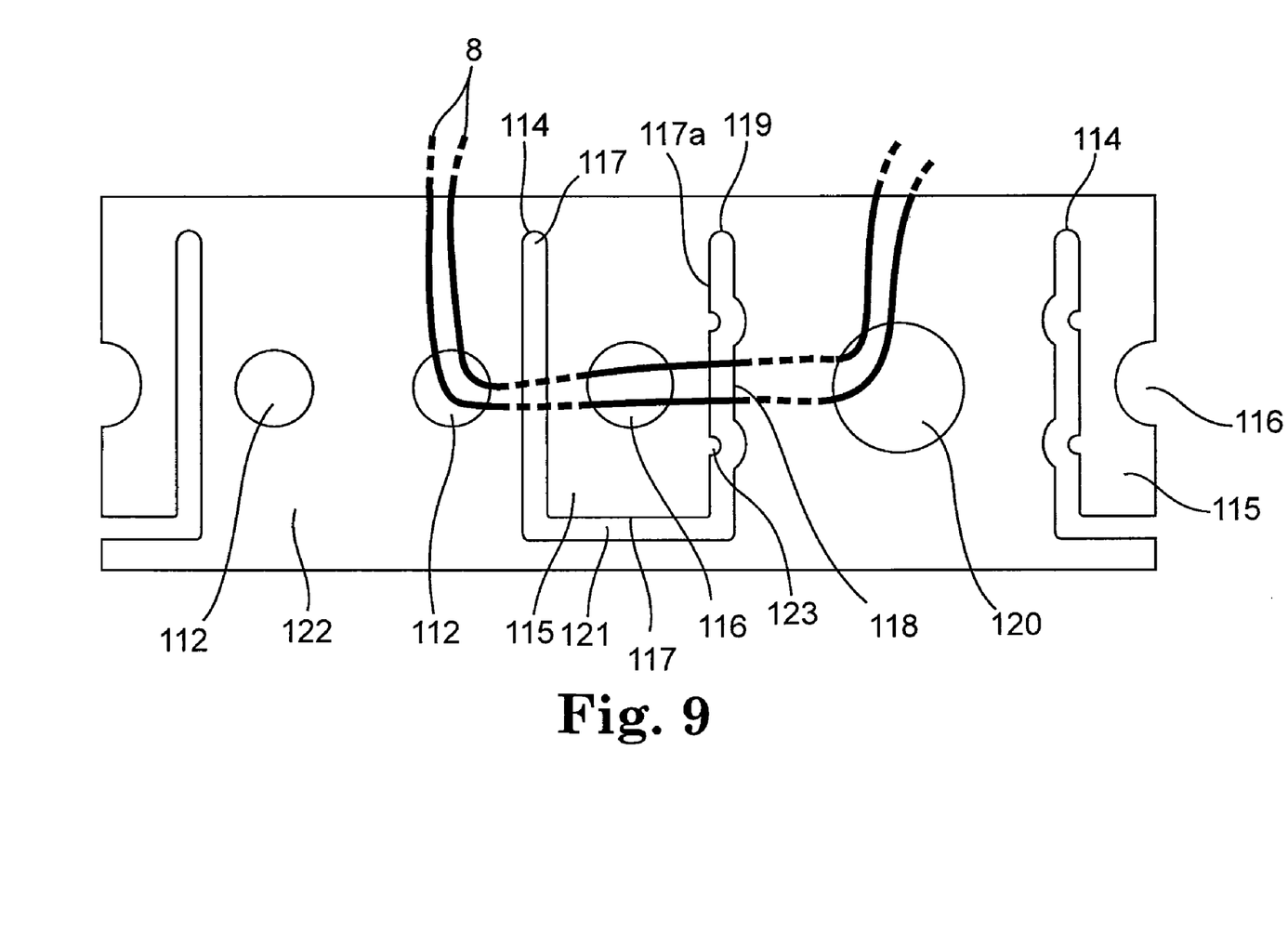
FIG. 9 is a flatten view of the external surface of the device of FIG. 8.
Figure 10:
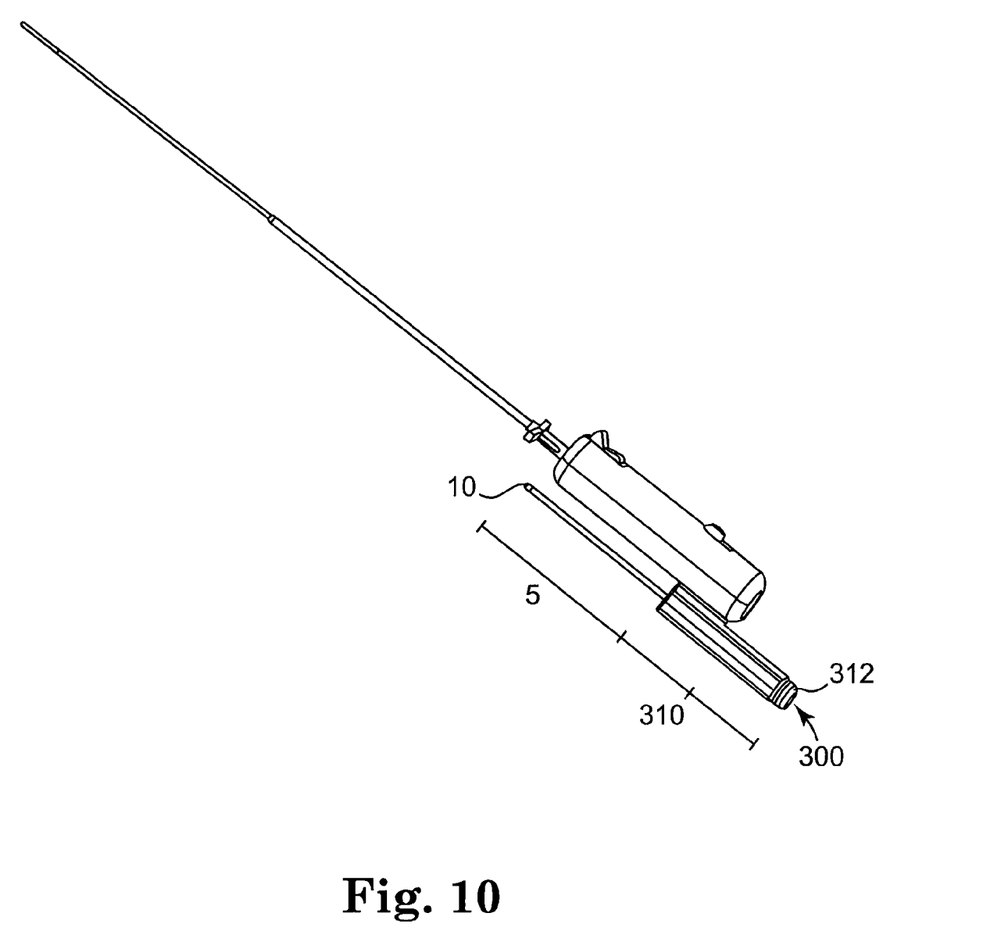
FIG. 10 is a perspective view of a vascular closure delivery device including a suture knot system in accordance with one embodiment.

Referring to FIGS. 8 and 9, a further embodiment of a suture lock device is illustrated. FIG. 8 illustrates the suture lock device as deployed. FIG. 9 illustrates a "rolled out" version of the suture lock device for purposes of illustration. The suture lock device 110 includes a base element 122 comprising one or more crimping means 114. As shown, the crimping means 114 are integral to the base element 122. As shown in FIG. 10, the base element 122 is substantially tubular and cylindrical, having a distal side 106 and a proximal side 108. When deployed, the proximal side is nearest to the vascular puncture while the distal side is farthest from the vascular puncture. In alternative embodiments, the base element 122 may be any suitable shape, for example, the base element 122 may be rectangular or spherical. The base element 122 extends along a longitudinal axis substantially perpendicular to a radial axis. The base element 122 includes an internal cavity 125 that extends through the device along the longitudinal axis.

A plurality of entrance apertures 112 and an exit aperture 120 are provided along the base element 122. The entrance apertures 112 are positioned along the proximal side 108 of the suture lock device 110 and the exit aperture 120 is positioned along the distal side 106 of the suture lock device 110 when deployed.

In the embodiment shown, two crimping means 114 are provided. Each crimping means comprises a suture clip 115, and a crimping slot 118 defined between the suture clip 115 and the base element 122. As shown, the suture clip 115 is a portion of the base element 122 cut along three walls 117, 117a and hinged along the fourth 119. Two notches 123 are provided along one wall 117a of the suture clip 115 to aid in preventing longitudinal migration of the sutures 8. The notches 123 maintain the sutures in a central position of the suture clip, as described more fully below. In alternative embodiments, the suture clip 115 may not be integral with the base element 122. Thus, for example, a portion of the base element 122 may be cut away and a separate suture clip 115 fixedly secured to the base element 122. A suture aperture 116 is provided on each suture clip 115.

Two pairs of sutures are threaded through the suture lock device 110. A first pair of sutures 8 is threaded into the central cavity 125 of the suture lock device 110 through a first entrance aperture 112a. The sutures 8 are extended under a first portion of the first suture clip 115a and threaded out through the suture aperture 116 of the suture clip. The sutures 8 are then threaded through the crimping slot 118 along wall 117a between notches 123, thereby reentering the central cavity 125. The sutures 8 are then threaded within the central cavity 125 to exit through the exit aperture 120.

Similarly, a second pair of sutures 8 is threaded into the central cavity 125 of the suture lock device 110 through a second entrance aperture 112b. The sutures 8 are extended under a first portion of the second suture clip 115b and threaded out through the suture aperture 116 of the suture clip. The sutures 8 are then threaded through the crimping slot 118 along wall 117a between notches 123, thereby reentering the central cavity 125. The sutures 8 are then threaded within the central cavity to exit trough the exit aperture 120.

The entrance apertures 112, suture apertures 116, crimping slots 118, and exit aperture 120 allow for the translational movement of the suture lock device 110 with respect to the suture filaments 8. The frictional engagement of the sutures with the suture lock device 100 is sufficient to retain the suture lock device 100 in contact with the vascular puncture. While the embodiment of FIGS. 10 and 11 is described specifically with reference to two pairs of suture filaments, it is to be appreciated than any suitable number of suture filaments may be used and even numbers of suture filaments are not necessary.

FIG. 10 illustrates a vascular closure delivery system including a suture knot system 300. The suture knot system 300 may be used to deploy the suture lock device 10 (or 50, 90, or 110). The suture knot system 300 includes a suture portion 5 and a handle 310. A tensioning knob 312 may be disposed at a proximal end of the handle 310. The suture lock device 300 may be provided at the distal end of the suture portion 5. Sutures extend from the surgical site, through the suture portion 5 and, optionally, through the handle 300 to the tensioning knob 312. The sutures travel through the handle 310 and the handle 310 acts as a pusher to push the suture lock device 10 to the surgical site. This engagement keeps the sutures substantially in tension while the suture lock device 10 is being deployed. The tensioning knob 312 may additionally be pulled or actuated to affirmatively tense the sutures. By keeping the sutures substantially in tension during suture lock device deployment, slack in the sutures between the suture site and the suture lock device as deployed is substantially avoided. The vascular closure delivery system and suture knot system 300 are more fully described in copending U.S. patent application Ser. Nos. 11/551,523, filed Oct. 20, 2006; and 11/551,635, filed Oct. 20, 2006, both herein incorporated by reference.

Although the invention has been described with reference to preferred embodiments, persons skilled in the art will recognize that changes may be made in form and detail without departing from the spirit and scope of the invention.

What is claimed is:

1. A suture attachment device for fastening multiple suture filaments at a wound or surgical site, comprising:
a lock body having:
 a proximal surface;
 a distal surface;
 an external wall extending from the proximal surface to the distal surface;
 a length defined between the proximal surface and the distal surface and extending along a longitudinal axis;
 a width extending along a radial axis, wherein the length is greater than the width;
 at least two separate and distinct suture passageways defined between the proximal surface and the distal surface, wherein each of the suture passageways comprise a proximal surface passageway and a distal surface passageway, the proximal surface passageway being accessible on the proximal surface of the lock body and the distal surface passageway being accessible on the distal surface of the lock body;
wherein the proximal surface passageway initiates on the proximal surface and terminates at a first aperture on the external wall, and the distal surface passageway initiates on the distal surface and terminates at a second aperture on the external wall, wherein each of the suture passageways are sized and shaped for receiving a suture filament such that the suture filament is threaded through the lock body.

2. The device of claim 1, wherein the proximal surface passageway and the distal surface passageway are offset by an acute angle with respect to the longitudinal axis.

3. The device of claim 1, wherein the proximal surface passageway and the distal surface passageway for a given suture passageway are aligned with respect to the longitudinal axis of the lock body.

4. The device of claim 1, wherein the lock body is substantially cylindrical in shape.

5. The device of claim 1, further comprising an outer sleeve sized and configured to fit over the lock body to compresses the suture filament against the external wall.

6. The device of claim 1, wherein the proximal surface passageway includes a proximal aperture defined in the proximal surface of the lock body.

7. The device of claim 6, wherein a diameter of the proximal surface passageway increases as it extends through the lock body from the proximal surface to the distal surface.

8. The device of claim 1, wherein the lock body is elastic.

9. A suture attachment device, comprising:
a lock body, including:
a proximal surface;
a distal surface;
an external wall extending from the proximal surface to the distal surface;
a plurality of suture passageways separated from each other, each passageway and comprising:
a proximal passageway extending from a proximal aperture on the proximal surface to a first side aperture on the external wall;
a distal passageway extending from a distal aperture on the distal surface to a second side aperture on the external wall;
an external portion extending along the external wall external of the lock body and between the first and second side apertures.

10. The suture attachment device of claim 9, wherein the distal and proximal surface are planar and the external wall is contoured.

11. The suture attachment device of claim 9, wherein a portion of each of the proximal passageway and distal passageway is open in a radial direction, and a portion of each of the proximal passageway and distal passageway is open in a longitudinal direction.

* * * * *